(12) United States Patent
Olek

(10) Patent No.: US 6,653,070 B1
(45) Date of Patent: Nov. 25, 2003

(54) GENOMIC ANALYSIS PROCESS AND AGENT

(75) Inventor: Alexander Olek, Berlin (DE)

(73) Assignee: GAG Bioscience Zentrum fur Umweltforschung und Technologie, Bremen (DE)

( * ) Notice: Subject to any disclaimer, the term of this patent is extended or adjusted under 35 U.S.C. 154(b) by 0 days.

(21) Appl. No.: 09/068,362

(22) PCT Filed: Nov. 8, 1996

(86) PCT No.: PCT/DE96/02169

§ 371 (c)(1),
(2), (4) Date: Jul. 17, 1998

(87) PCT Pub. No.: WO97/17461

PCT Pub. Date: May 15, 1997

(30) Foreign Application Priority Data

Nov. 9, 1995  (DE) .......................................... 195 43 065

(51) Int. Cl.⁷ ................................................. C12Q 1/68
(52) U.S. Cl. ........................... 435/6; 435/7.1; 435/91.1; 435/91.2; 435/287.2; 536/22.1; 536/23.1; 536/24.3; 536/24.31; 536/24.32; 536/24.33
(58) Field of Search ......................... 435/6, 91.1, 91.2; 536/23.1, 24.3, 24.31, 24.32, 24.33, 25.3, 25.4

(56) References Cited

U.S. PATENT DOCUMENTS

| | | | | |
|---|---|---|---|---|
| 4,683,202 A | * | 7/1987 | Mullis | |
| 5,498,545 A | * | 3/1996 | Vestal | |
| 5,545,531 A | * | 8/1996 | Rava et al. | |
| 5,605,798 A | * | 2/1997 | Koster | ............................ 435/6 |
| 5,753,438 A | * | 5/1998 | Drayna et al. | .................. 435/6 |

FOREIGN PATENT DOCUMENTS

| WO | WO89/10977 | * | 11/1989 |
|---|---|---|---|
| WO | WO93/17126 | * | 9/1993 |

OTHER PUBLICATIONS

Morral et al Genomics vol. 13 pp. 1362–1364 1992.*
Liu et al Analytical Chemistry vol. 67 pp. 3482–3490 1995.*
Zaluzec American Soc. for Mass Spectrometry vol. 5 pp. 2330–237 1994.*
Guo et al NAR vol. 22 No. 24 pp. 5456–5465, 1994.*
Saiki et al PNAS vol. 86 pp. 6230–6234, 1989.*

* cited by examiner

Primary Examiner—Jeffrey Siew
(74) Attorney, Agent, or Firm—Norris McLaughlin & Marcus

(57) ABSTRACT

A genomic analysis process is disclosed, in particular for analysing and localising hereditary properties in the genome. This process has applications in a large number of fields, in particular in medicine, agriculture, forensic medicine and fundamental research. This genomic analysis process is characterised in that the amplification products of microsatellites form genomic DNA samples are immobilised. The genomic DNA samples are separated on defined positions of the matrix, before or after being amplified into individual microsatellite markers, the individual positions are evaporated in a mass spectrometer and their molecular weight is determined.

11 Claims, No Drawings

GENOMIC ANALYSIS PROCESS AND AGENT

DESCRIPTION

The invention discloses a genomic analysis process, in particular for analysing and localising hereditary properties in the genome. This process has applications in a large number of fields, in particular in medicine, agriculture, forensic medicine and fundamental research.

STATE OF THE ART

1.1 Definition of Microsatellites

Here, the term of a microsatellite is used in the following sense: a microsatellite is an oligonucleotide repeat showing various alleles between the individual chromosomes of a species, i.e. is polymorphic. The various alleles differ by their length, i.e. their molecular weight. Each microsatellite is flanked—and thus also defined—by two non-polymorphic DNA sequences appearing only once which as hybridisation partners are used by the primers for carrying out a polymerase chain reaction.

1.2 Applications of Microsatellite Markers

Microsatellite markers are a main instrument of modern genetic analysis.

1.2.1

On the one hand, these markers are applied to detect after a meiotic cell division took place which of the two alleles was transferred to a descendant in a genomic locus associated with the respective marker.

This principle is used in the coupling analysis: If microsatellite marker alleles, together with a genetic defect, are inherited with a frequency above average in a family with several persons suffering from a hereditary disease the defect locus and the microsatellite marker are physically coupled, i.e. they are situated close to each other in the genome.

With localising of a microsatellite in a genome being known this information allows to draw conclusions as to the position of the gene(s) responsible for the defect. For the time being, two methods of the coupling analysis are applied in practise:

the so-called lod-score method based on an analysis of a few up to numerous large families involving a few persons affected, the "affected relative method" (ARM) based on a comparison of a multitude of pairs of related test persons.

In both cases, haplotyping of numerous persons is required. By haplotyping we understand detecting for each person to be analysed which of the alleles of each of the polymorphic marker is contained in the genome of the test person. Today, nearly exclusively microsatellite markers are typified. This is due to the fact that they are analysed most reliably and rapidly (see semiautomatization below) and may be identified most efficiently. That is why according to the state of the art more than 5000 of these markers are available for man and all systems available on the market for carrying out the coupling analysis are based on these markers. To establish with some degree of certainty a coupling of a microsatellite to form genes which are not responsible for a defect at least 300–600 pairs of affected relatives will have to be examined with always at least 400 microsatellites in the case of a disease not inherited according to Mendel's pattern (This group of defects and predispositions is the main target of our method).

Genotypifying of by far more test persons with essentially more markers would be ideal to get a possibly exact idea of the genomic loci after establishing the coupling groups. In this second step markers covering the regions detected in the first step by coupling with an essentially higher resolution are applied.

The most up-to-date and fastest approach to genotypification with microsatellites is using florescence-marked microsatellite primers and determining the size of microsatellite alleles by means of a semiautomatic sequencer. This method allows to analyse up to 24, yet on an average, only 15 microsatellites on an electrophoresis gel path (with up to 48 patris per gel) which, however, means that in the best case 1000–2000 of such gels are used to establish a coupling applying the ARM (Vignal, A. et al., 1993; Methods in Molecular Genetics: Gene and Chromosome analysis. Academic Press, San Diego. Pages 211–221 and Davies, J. L. et al., 1994; Nature 371: 130–136). This means, that a sequencer would be utilised to the full for at least one year in the ideal case. The costs of such a coupling analysis including personnel costs may total up to a few millions of DM. In the last few years the interest of the participating scientists was focussed ever more on frequently occurring, polygenic, multifactorial or multigene diseases (Lathrop, G. M., 1993; Current Opinion in Biotechnology 4:678–683). The more components will participate in the development of a disease the more persons have to be genotypified to establish a coupling. Thus, the expenses and costs will go up exponentially with the complexity of a disease. That means, that a coupling analysis for the so-called widespread diseases will be by far more expensive than has been mentioned before.

In the case of useful and domestic animals, yet also plants, the coupling analysis is the most promising instrument to localise valuable breeding properties in the genome and to isolate the respective genes.

This allows the breeder to concentrate positive properties and to minimise negative properties. The breeding strategy common so far allows to assess a breeding success only after a few generations have grown up. In addition, the breeding result is not foreseeable in most of the cases.

Notably, in the case of positive properties such as stable resistances to pathogens and resistance to cold, as a rule, comprehensive genetic parameters are concerned requiring an expenditure on the human genetic problems as described above.

1.2.2

Secondly, there may be detected whether a certain allele of a microsatellite is contained at all in two genomes to be compared which after having analysed sufficient markers allows to confirm or to exclude a relation. As to man, this question arises e.g. in the case of paternity tests or in forensic medicine to exclude or identify offenders. In addition to typifying HLA surface antigenes here, the use of highly polymorphic microsatellite markers gained acceptance in practice and replaced largely genetic dactylograms (multiloci).

Also in the case of useful animals the proof of origin by means of a microsatellite analysis was declared the standard method, on international scale.

For these applications, as a rule, about 10 microsatellite markers are analysed. The whole proof including evaluation will require about 2 days.

For the time being, the costs of such an analysis total at least DM 50, also in the case of the quantity of samples being large.

2. Disadvantages of the Technology Generally Applied Today

2.1 Coupling Analysis of Complex Diseases of Man

An analysis of up to a few thousands of pairs of related persons affected is required for analysing widespread, multifactorial diseases such as e.g. arteriosclerosis, diabetes II, Alzheimer or schizophrenia as it is, as a rule, not possible to apply the lod-score method. The main reasons for that are a lack of large families involving sufficient affected persons and a lack of a hereditary transmission model process. That is why only extremely few research groups are worldwide in a position to carry out such an analysis. The expenses of such an analysis are very high, as described above in greater detail. Yet, the equipment is also expensive because the production costs of fluorescence-marked primers are extremely high. To synthesize these primers we depend on a few companies.

A principle disadvantage of the electrophoretic separation of fluorescence-marked DNA fragments consists in the fact that a proper automatic sample analysing is not possible. Automating the evaluation is still more difficult. The software designed by the producers of sequencers is necessarily insufficient. Basically, efforts are made to automate a method which is not to be automated with the aid of most complicated computers.

A decisive disadvantage of the common electrophoretic methods is that an absolute determination of the size of fragments is not possible.

This means, that expensive and finally not always reliable calibration procedures are required. Attempts are made to eliminate these problems partly by using cloned alleles as internal standards. This might be achieved also limitedly.

Yet, the circumstance that the mobility of the DNA fragments corresponding to the alleles depends on various parameters of sample analysing, thus e.g. marking and individual conditions of reaction in the PCR. Thus, the decisive measurable variable of a microsatellite analysis, namely the length of the fragments, has to be based on a number of auxiliary variables. Yet, it is only possible to assign a certain frequency to a reliably identified allele in an analyses of identity or origin. However, the reliability of the data gained in an analysis depends nearly exclusively on the last-mentioned.

2.2 Coupling Analysis in the Case of Useful Animals and Plants

As a rule, localising of genes of useful and domestic animals and plants which control valuable breeding properties is impossible owing to the extremely high price of the study. The vast majority of the interesting breeding properties has a polygenic background. Thus, a very expensive coupling analysis would be required.

2.3 Proof of Origin of Useful Animals

Also here, the decisive factor is the price of an analysis. A proof of origin of useful animals will be appropriate if each animal will be individually genotypified or at least analysing of a large quantity of random samples will be possible. The price of a conventional microsatellite analysis has an essential share in the price of an animal for most of the species of useful animals.

Neither breeders nor consumers will be prepared to accept an essential increase in the price of useful animals which would make a microsatellite analysis of these animals senseless from a market economy perspective.

3. The Task of the Invention

The invention is based on the task to rationalise the genomic analysis, in particular localising hereditary properties in the genome, thus allowing its application also in cases where previous methods are not taken into consideration for reasons of costs.

4. The Essence of the Invention

The process according to the invention is characterised by the principle claim, the subclaims are preferential variants. As an essential component it envisages analysing of microsatellites by means of mass spectrometry. In this connection, the unique sequences flanking each of the microsatellites as a single-line DNA shall be immobilised on a solid matrix. The matrix is subdivided in a way that each single-line DNA defining a microsatellite is immobilised in a certain position of this matrix. If a mixture of amplified microsatellites in a single-line state is placed on this matrix the available alleles of each of the microsatellites hybridise only exactly in the position of the matrix where the primer sequence defining the microsatellite had been marked.

The distinctive feature of this variant of the method according to the invention is that, in principle, only one PCR batch is required to amplify all microsatellites (in the ideal case) which altogether are brought into contact with the matrix for hybridisation (multiplex PCR with all microsatellite primers used). Even if this ideal case will not be given and not all microsatellites may be amplified in the same reaction by far less reactions will be required to amplify all microsatellites which are e.g. necessary to carry out a coupling analysis.

Fact is that limiting of the present methods (see state of the art, multiplex PCR with fluorescence-marked primers) is mainly due to the fact that not more than maximally 24 fragments not overlapping on a gel path may be dissolved. According to the invention hybridisation of the microsatellite amplification products is followed by a gradual loosening of the DNA from the individual positions of the matrix and placing the DNA on the probe of the mass spectrometer. This procedure may be automatically implemented at a very high speed (see e.g. Koester, Human Genome Mapping Symposium, Cold Spring Harbour Laboratory, 1995). Latest approaches to DNA sequencing by means of hybridisation and mass spectrometric analysis allow to place a few hundred of fragments within milliseconds onto a mass spectrometer. The matrix may represent a solid phase where oligonucleotides are immobilised by a covalent bonding, hybridisation or other types of physical or chemical bonding. It may be also represented by microtitration plates or other containers in the individual reaction vessels of which the locus-specific oligonucleotides are immobilised.

A further form of implementing the invention is to amplify the microsatellites individually, in a very small reaction volume.

New types of nanopipetting systems allow a computer-controlled preparation of reactions on a scale of less than 1 $\mu$l. Thus, hundreds or thousands of PCR may be effected simultaneously on miniaturised microtitration plates or in similar miniaturised reaction vessels. The difference between this and the above-mentioned variants is that though multiplex PCR (amplification of many, up to hundreds of microsatellites) may be effected (see state of the art) it may in practice cause problems relating to the reproducibility of the results if extremely complex reactions (a few hundreds of primer pairs) take place.

That is why the following analysing strategy of microsatellites in a mass spectrometer is to be patented: computer-controlled nanolitre pipettes supply PCR reaction vessels of a dimension <1 $\mu$l. These pipettes place the individual marker-loci amplification products onto a matrix absorbing the amplified DNA in a way as to supply discrete positions of the matrix with individual amplification products without resulting in a mixing of the samples of adjacent positions on the matrix. Various commercially available matrices have this quality (e.g. nitrocellulosis or nylon). Yet, also placing of microsatellites on surfaces of a new type and their subsequent analysing in a mass spectrometer is object of the invention. Modern pipetting systems are in a position to place a few thousands of samples in the nanolitre range per $cm^2$. As the microsatellites are amplified individually a defined microsatellite amplification product may be placed on each defined position of the matrix. The amplification products from this matrix are evaporated one after the other and analysed in a mass spectrometer. That is why the two variants of execution provide similar possibilities: microsatellite amplification products are immobilised in defined positions in a most confined space the molecular weight of which is subsequently determined in a mass spectrometer.

In this connection, automation is striven for, yet analysing of microsatellites in a mass spectrometer shall be patented, in general. The invention involves also mass spectrometric analysing of reactions resulting directly from microsatellite amplifications. Without immobilising the microsatellites previously on a matrix applying one of the two process variants mentioned analysing microsatellite markers in a mass spectrometer manually would be of advantage as against usual methods.

In principle, each of the various mass spectrometric methods available for the analysing method described here would be suited if it will allow to investigate high-molecular biomolecules.

The mass spectrometric method is based on placing the microsatellite marker amplification product onto a non-volatile support. Thereupon, the placed DNA is converted into a vapour phase and accelerated by an electric or magnetic field. The path. of the accelerated DNA passes an electric or magnetic field deflecting the DNA from the straight path. The degree of this deflection depends on the charge (in the case of DNA, constant per atomic weight unit) and the molecular weight of the DNA. The degree of deflection and thus the absolute molecular weight may be determined through the position of the impact of the DNA molecule on a detector.

As a mass spectrometric analysis is in any case evaluated directly in a digitalised form in a connected computer the molecular weight of all microsatellite alleles may be transmitted directly to a genetic analysing program.

5. Advantages of the Process According to the Invention

The process is cheaper than any other process for analysing microsatellites. It is exacter; it allows an objective mass determination with an extremely high resolution.

Seconds instead of hours are required for analysing a locus. Specially marked DNA sondes or primers connected with remarkable costs are not required. Though mass spectrometers are similar costly as automatic sequencers analysing is so fast that also technologically insufficiently equipped institutions can order coupling analyses as service.

In view of these advantages a coupling analysis in connection with a genomic analyse of man will be made easier, accelerated and be by far cheaper. This is a precondition for analysing very complex genetic defects and predispositions. In addition, the study of animal models of human diseases (where an unlimited number of individuals is available for analysing as systematic crossbreeding is possible) will be facilitated so remarkably that this approach will gain essentially in practicability.

The routine localising of valuable breeding properties in useful animals will become possible only by applying the process according to the invention. For the time being, the price and expenditure of time on such analysis exceed the benefit of it, for analytical reasons (see above). The same refers also to mapping of e.g. resistances and other properties of useful plants. Only if an efficient microsatellite analysing method will be on the market systematic genome projects will provide the prerequisite for entering routine plant properties on a map.

The analysis of origin and identity of man will become technically and legally more reliable. A determination of the absolute size of microsatellite markers is made possible, thus eliminating a principle problem involved in this method in this area.

Only the invention allows to analyse the origin and identity of most of the useful animals and plants as, for the first time, the price of such an analysis has no significant share in the market value of the animal/plant.

An essential advantage is what all information is directly transmitted from the mass spectrometer to a common analysing software by means of interfaces designed for this to establish e.g. a coupling. This saves the costs and insecurities of a manual step which today is indispensable.

What is claimed is:

1. A method for analyzing the microsatellite DNA content in genomic DNA, the method comprising the steps of, a) performing a polymerase chain reaction on genomic DNA to provide a sample having one or more distinct amplified nucleotide sequences, wherein an amplified sequence comprises at least one microsatellite DNA sequence or portion thereof, and optionally, a DNA sequence flanking the microsatellite DNA sequence;

b) preparing a support matrix having defined positions wherein the preparing comprises immobilizing in a defined position one or more nucleotide sequences capable of hybridizing with an amplified sequence in said sample, c) contacting the one or more distinct amplified nucleotide sequences with the prepared support matrix under conditions conducive to hybrid formation between an amplified nucleotide sequence and a matrix-immobilized nucleotide sequence;

d) dissociating the one or more hybridized amplified nucleotide sequences from the at least one defined area of the support matrix and subjecting the one or more amplified nucleotide sequences to mass spectrometry whereby a size distribution of amplified sequences that hybridized to the define region is obtained.

2. The method of claim 1, wherein the at least one distinct nucleotide sequence comprises one or more sequences corresponding to genomic sequences that flank a particular microsatellite DNA.

3. The method of claim 1, wherein the one or more amplified nucleotide sequences or portions thereof, are sequenced.

4. The method of claim 1, wherein the solid support matrix may comprise a membrane or matrix material suitable for performing nucleic acid hybridization procedures.

5. The method of claim 1, wherein the solid support matrix may be a multiwell plastic assay or microtiter dish.

6. The method of 1 wherein the solid support matrix comprises a material selected from the group consisting of nylon, nitrocellulose, glass, ceramic or metal.

7. The method of claim 1, wherein the defined area of the matrix comprises one immobilized nucleotide sequence.

8. The method of claim 1, wherein the defined area of the matrix comprises two or more immobilized nucleotide sequences.

9. The method of claim 1, wherein at least one of the matrix-immobilized nucleotide sequence hybridizes to a repetitive nucleotide sequence, wherein said repetitive sequence is indicative of a genomic microsatellite locus.

10. The method of claim 1, wherein the dissociating of the amplified nucleotide sequence from the matrix is performed prior to introducing the matrix containing the amplified nucleotide sequence into the mass spectrometer.

11. The method of claim 1, wherein the dissociating of the amplified nucleotide sequence from the matrix occurs concomitantly or after introducing the matrix containing the amplified nucleotide sequence into the mass spectrometer.

* * * * *